(12) United States Patent
Zou et al.

(10) Patent No.: US 9,610,057 B2
(45) Date of Patent: Apr. 4, 2017

(54) SYSTEM AND METHOD FOR DETERMINING X-RAY EXPOSURE PARAMETERS

(71) Applicant: General Electric Company, Schenectady, NY (US)

(72) Inventors: Yun Zou, Clifton Park, NY (US); David Allen Langan, Clifton Park, NY (US); Hao Lai, Rexford, NY (US); Rowland Frederick Saunders, Hartland, WI (US); John Michael Sabol, Sussex, WI (US); Guillermo Sander, Ridgewood, NJ (US)

(73) Assignee: General Electric Company, Niskayuna, NY (US)

( * ) Notice: Subject to any disclaimer, the term of this patent is extended or adjusted under 35 U.S.C. 154(b) by 186 days.

(21) Appl. No.: 14/552,546

(22) Filed: Nov. 25, 2014

(65) Prior Publication Data

US 2015/0359502 A1    Dec. 17, 2015

Related U.S. Application Data

(63) Continuation-in-part of application No. 14/305,410, filed on Jun. 16, 2014.

(51) Int. Cl.
*H05G 1/64*    (2006.01)
*A61B 6/00*    (2006.01)
*G06T 11/00*    (2006.01)

(52) U.S. Cl.
CPC ............ *A61B 6/542* (2013.01); *A61B 6/4405* (2013.01); *A61B 6/469* (2013.01); *A61B 6/482* (2013.01);

(Continued)

(58) Field of Classification Search
CPC ........... A61B 6/542; A61B 6/545; A61B 6/58; A61B 6/488; A61B 6/482; G01N 23/04;

(Continued)

(56) References Cited

U.S. PATENT DOCUMENTS 5,881,127 A    3/1999 Molloi et al.
6,292,536 B1   9/2001 Chichereau et al.
(Continued)

FOREIGN PATENT DOCUMENTS

EP    0990419 A1    4/2000
EP    1151645 B1    10/2011

OTHER PUBLICATIONS

PCT Search Report and Written Opinion issued in connection with related PCT Application No. PCT/US2015/035760 on Dec. 22, 2015.

(Continued)

*Primary Examiner* — Jurie Yun
(74) *Attorney, Agent, or Firm* — Melissa K. Dobson

(57) ABSTRACT

In accordance with one aspect of the present system, a dual energy X-ray imaging system includes a communication module configured to receive a pre-shot image from a detection circuitry and receive one or more pre-shot parameters from a source controller of the dual energy X-ray imaging system. The dual energy X-ray imaging system further includes an analysis module configured to determine one or more image characteristics of the pre-shot image. The dual energy X-ray imaging system further includes a determination module configured to calculate a first and a second set of main-shot parameters based on the one or more pre-shot parameters and the one or more image characteristics of the pre-shot image. The determination module is (Continued)

further configured to send the one or more main-shot parameters to the source controller of the dual energy X-ray imaging system.

17 Claims, 4 Drawing Sheets

(52) U.S. Cl.
CPC ............ *A61B 6/488* (2013.01); *A61B 6/5217* (2013.01); *A61B 6/5235* (2013.01); *A61B 6/544* (2013.01); *A61B 6/545* (2013.01); *A61B 6/563* (2013.01); *G06T 11/005* (2013.01); *A61B 6/4035* (2013.01); *A61B 6/5205* (2013.01); *G06T 2211/408* (2013.01)

(58) Field of Classification Search
CPC ........ G01N 23/08; G01N 23/083; G06T 5/50; H05G 1/46; H05G 1/32; H05G 1/34
USPC ..... 378/16, 62, 98.9, 98.11, 98.12, 109–112, 378/207
See application file for complete search history.

(56) References Cited

U.S. PATENT DOCUMENTS

| | | | |
|---|---|---|---|
| 6,501,819 B2 | 12/2002 | Unger et al. | |
| 6,556,655 B1 | 4/2003 | Chichereau et al. | |
| 6,795,526 B2 | 9/2004 | Kump et al. | |
| 6,827,489 B2 | 12/2004 | Nicolas et al. | |
| 7,292,675 B1 | 11/2007 | Li et al. | |
| 7,313,224 B1 | 12/2007 | Saunders | |
| 7,313,225 B2 | 12/2007 | Mertelmeier | |
| 7,342,999 B2 | 3/2008 | Johansson et al. | |
| 7,431,500 B2 | 10/2008 | Deych et al. | |
| 8,744,041 B2 * | 6/2014 | Smith .................... | A61B 6/025 378/37 |
| 2002/0075997 A1 | 6/2002 | Unger et al. | |
| 2002/0085672 A1 | 7/2002 | Ganin et al. | |
| 2003/0081734 A1 | 5/2003 | Nicolas et al. | |
| 2003/0165216 A1 | 9/2003 | Walker et al. | |
| 2007/0297569 A1 | 12/2007 | Saunders | |
| 2009/0010384 A1 | 1/2009 | Jing et al. | |
| 2009/0268865 A1 | 10/2009 | Ren et al. | |
| 2011/0019891 A1 | 1/2011 | Puong et al. | |
| 2012/0051522 A1 | 3/2012 | Nishino et al. | |
| 2012/0087474 A1 | 4/2012 | Foos et al. | |
| 2012/0128125 A1 | 5/2012 | Jabri et al. | |
| 2012/0155609 A1 | 6/2012 | Lemminger et al. | |
| 2012/0160918 A1 | 6/2012 | Negro | |
| 2013/0022170 A1 | 1/2013 | Cho | |
| 2013/0148782 A1 | 6/2013 | Tajima | |
| 2013/0243283 A1 | 9/2013 | Kotchou et al. | |
| 2013/0301799 A1 | 11/2013 | Kang et al. | |
| 2014/0064444 A1 | 3/2014 | Oh et al. | |
| 2014/0119506 A1 | 5/2014 | Kang et al. | |
| 2015/0359498 A1 * | 12/2015 | Zou ........................ | A61B 6/469 378/62 |
| 2016/0007943 A1 * | 1/2016 | Hoernig ................. | A61B 6/482 378/37 |

OTHER PUBLICATIONS

"Gentle Touch. Brilliant Image. Mammography Solutions", Fujifilm Medical Systems Product Profiles, pp. 1-15, Ref. No. XB-960E, Fujifilm Corporation, Tokyo, Japan, 2014.

* cited by examiner

SYSTEM AND METHOD FOR DETERMINING X-RAY EXPOSURE PARAMETERS

CROSS REFERENCE TO RELATED APPLICATIONS

This Application is a continuation-in-part of U.S. patent application Ser. No. 14/305,410, entitled "SYSTEM AND METHOD FOR DETERMINING X-RAY EXPOSURE PARAMETERS," filed on Jun. 16, 2014, which is herein incorporated by reference.

FIELD OF INVENTION

The subject matter disclosed herein generally relates to X-ray imaging systems. More specifically, the subject matter relates to systems and methods for determining X-ray exposure parameters.

BACKGROUND

X-ray imaging systems, for example, digital radiography (RAD) systems, mammography systems, computed tomography systems, and the like, generate an image of an object by projecting an X-ray beam towards the object using an X-ray source and capturing the X-ray beam that has passed through the object using an X-ray detector. Recently, X-ray imaging systems generate one or more images of the object based on a dual energy technology. Such dual energy X-ray imaging systems sequentially project two X-ray beams (e.g., a high energy X-ray beam and a low energy X-ray beam) and process the images corresponding to the dual X-ray beams to generate one or more final X-ray images of the object. The exposure parameters (e.g., peak kilovoltage and milliampere second values) that define the X-ray beam generated by the X-ray source are often determined either manually by an operator or by a computing device using, for example, automatic exposure control (AEC) methods.

Manual methods often generate low quality images (e.g., images with low signal to noise ratio), since the determination of exposure parameters is subjective and dependent on, for example, the skill and experience of the operator. This is problematic, especially in dual energy X-ray imaging systems, since the processing of such low quality images leads to the generation of even lower quality or final X-ray images. In some AEC methods, a computing device controls the exposure parameters based on information received from an ionization chamber coupled with the X-ray detector. In some other AEC methods, a computing device controls the exposure parameters based on a preliminary image captured by the X-ray detector using a low dose X-ray beam. The implementation of such AEC methods on current X-ray imaging systems (e.g., mobile RAD systems) is problematic as they either lack the ionization chamber or have X-ray detectors which cause long time delays by wirelessly transmitting the preliminary images to the computing device.

Thus there is a need for an enhanced system and method for determining X-ray exposure parameters.

BRIEF DESCRIPTION

In accordance with one aspect of the present system, a dual energy X-ray imaging system includes a communication module configured to receive a pre-shot image from a detection circuitry and receive one or more pre-shot parameters from a source controller of the dual energy X-ray imaging system. The dual energy X-ray imaging system further includes an analysis module configured to determine one or more image characteristics of the pre-shot image. The dual energy X-ray imaging system further includes a determination module configured to calculate a first and a second set of main-shot parameters based on the one or more pre-shot parameters and the one or more image characteristics of the pre-shot image. The determination module is further configured to send the one or more main-shot parameters to the source controller of the dual energy X-ray imaging system.

In accordance with one aspect of the present technique, a method includes receiving a pre-shot image from a detection circuitry of a dual energy X-ray imaging system and receiving one or more pre-shot parameters from a source controller of the dual energy X-ray imaging system. The method further includes determining one or more image characteristics of the pre-shot image. The method further includes calculating a first and a second set of main-shot parameters based on the one or more pre-shot parameters and the one or more image characteristics of the pre-shot image. The method also includes sending the first and the second set of main-shot parameters to the source controller of the dual energy X-ray imaging system.

In accordance with one aspect of the present technique, a method includes receiving a pre-shot image from a detection circuitry of a dual energy X-ray imaging system and receiving one or more pre-shot parameters from a source controller of the dual energy X-ray imaging system. The method further includes determining one or more image characteristics of the pre-shot image. The method further includes calculating a first set of main-shot parameters based on the one or more pre-shot parameters and the one or more image characteristics of the pre-shot image. The method further includes receiving a first main-shot image corresponding to the first set of main-shot parameters. The method also includes calculating a second set of main-shot parameters based on at least one of the pre-shot parameters, the one or more image characteristics of the pre-shot image, and one or more image characteristics of the first main-shot image. The method also includes sending the second set of main-shot parameters to the source controller of the dual energy X-ray imaging system.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
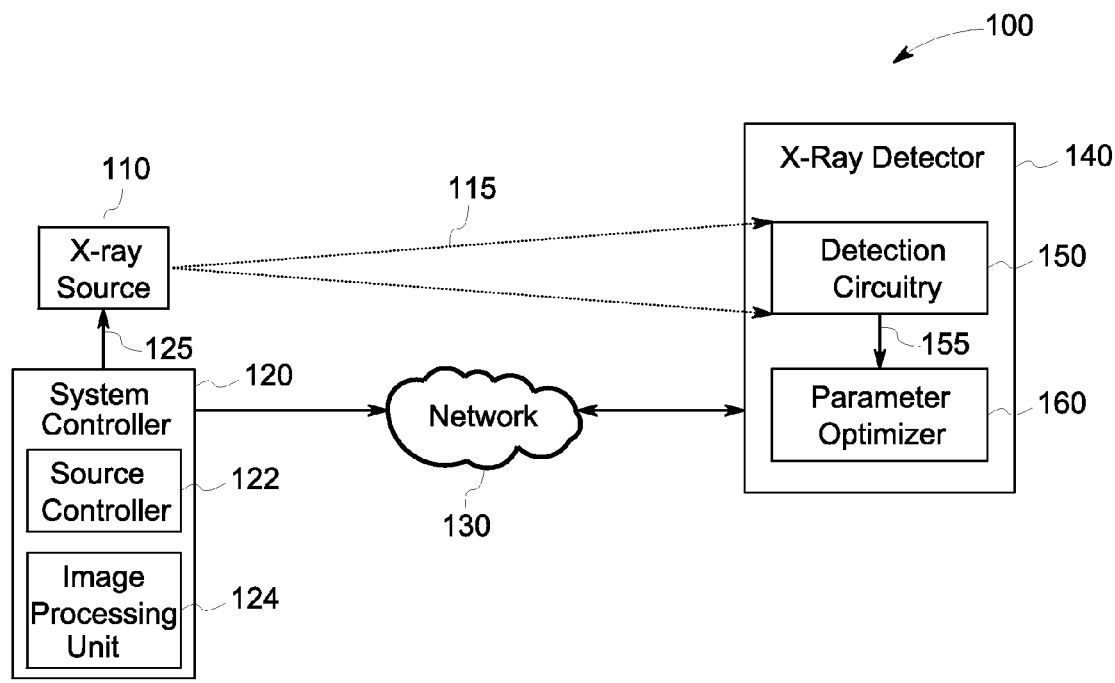
FIG. 1 is a block diagram illustrating a system for determining X-ray exposure parameters according to one embodiment.

A system and method for determining X-ray exposure parameters are described herein. FIG. 1 illustrates a block diagram of a dual energy X-ray imaging system 100 (e.g., a mammography system, a RAD system, a computed tomography system, a tomosynthesis system, and the like) configured to generate images of an object (e.g., a human patient), according to one embodiment. The system 100 includes an X-ray source 110, a system controller 120, and an X-ray detector 140. The system controller 120 and the X-ray source 110 are communicatively coupled via signal line 125. The system controller 120 and the X-ray detector 140 are communicatively coupled via a network 130. In the illustrated embodiment, the system 100 is configured to generate a pre-shot image of the object using a low dose X-ray beam that is defined by pre-shot X-ray exposure parameters. The system 100 is further configured to determine a first and a second set of main-shot X-ray exposure parameters based at least on the pre-shot image, generate a first and a second main-shot image corresponding to the first and the second set of main-shot parameters, and generate a final image (e.g., a bone image, soft tissue image, and the like) of the object based on the first and the second main-shot image.

For the purpose of clarity and convenience, the pre-shot X-ray exposure parameters and the main-shot X-ray exposure parameters, are referred to herein, as the pre-shot parameters and the main-shot parameters respectively. The pre-shot parameters include, for example, x-ray tube focal spot size, a pre-shot peak kilovoltage (kVp) of the X-ray source 110, a pre-shot milliampere seconds (mAs) of the X-ray source 110, a patient size, an anatomical region of the patient (e.g., chest, leg, and the like), a view type (e.g., lateral view, frontal view, and the like), and a distance between the X-ray source 110 and the X-ray detector 140. The first and the second set of main-shot parameters include, for example, a first and a second main-shot kVp of the X-ray source 110, a first and a second main-shot mAs of the X-ray source 110, a first and a second main-shot milliampere (mA) of the X-ray source 110, a first and a second main-shot exposure time of the X-ray source 110, a first and a second main-shot X-ray focal spot size, and a first and a second main-shot X-ray filter respectively.

The X-ray source 110 may be any type of device that is configured to generate and direct an X-ray beam 115 towards the X-ray detector 140 and an object positioned between the X-ray source 110 and the X-ray detector 140. The X-ray source 110 includes an X-ray tube comprising an anode and a cathode that emits electrons and generates the X-ray beam. The X-ray source 110 generates a pre-shot X-ray beam, a first main-shot X-ray beam, and a second main-shot X-ray beam based on the pre-shot parameters, a first set of main-shot parameters, and a second set of main-shot parameters respectively. The X-ray source 110 receives the pre-shot and the main-shot parameters from the system controller 120 via signal line 125.

The system controller 120 may be any type of computing device that is configured to control the operation of the system 100. In the illustrated embodiment, the system controller 120 includes a source controller 122 and an image processing unit 124. The source controller 122 is configured to control the operation of the X-ray source 110 based on the pre-shot and the main-shot parameters. The source controller 122 receives one or more pre-shot parameters from, for example, an operator of the system 100 as user input. For example, the operatory may input the pre-shot kVp as 10 kVp, the pre-shot mAs as 3 mAs, the distance between the X-ray source 110 and the X-ray detector 140 as 1 meter, the patient size as 10 cm or in general Large, Medium and Small Adults, and the like, the view type as postero-anterior, antero-posterior, lateral, and the like. The operator may define the pre-shot parameters based on, for example, previously generated clinical data, the set-up of the system 100, the patient, the anatomy to be imaged and the like. The operator may not define all the pre-shot parameters. Some pre-shot parameters may be determined by the system 100 based on inputs received from the operator. The source controller 122 sends the pre-shot parameters to the X-ray source 110 for generating the pre-shot X-ray beam. The source controller 122 also sends the pre-shot parameters to the X-ray detector 140.

In one embodiment, the operator may modify the pre-shot parameters based on a notification received from the X-ray detector 140. In such an embodiment, the source controller 122 sends the modified pre-shot parameters to the X-ray source 110 for re-generating the pre-shot X-ray beam. The notification received from the X-ray detector 140 is described below in further detail with reference to FIG. 2. In a further embodiment, the process can be automated or semi-automated, wherein the source controller 122 receives the pre-shot parameters from memory or from a processing section that interpolates certain pre-shot parameters based on system configurations, a priori data and general thresholds.

The source controller 122 further receives the first and the second set of main-shot parameters from the X-ray detector 140. For example, the source controller 122 receives the first main-shot kVp as 60 kVp and the first main-shot mAs as 10 mAs (i.e., low energy main-shot parameters). The source controller 122 receives the second main-shot kVP as 120 kVp and the second main-shot mAs as 10 mAs (i.e., high energy main-shot parameters). The source controller 122 sends the first and the second set of main-shot parameters to the X-ray source 110 for generating the first main-shot X-ray beam (i.e., low energy X-ray beam) and the second main-shot X-ray beam (i.e., high energy X-ray beam) respectively. Although, in the above example, the first and the second set of main-shot parameters are described as low and high energy main-shot parameters respectively, in another example, the first and the second set of main-shot parameters are described as high and low energy main-shot parameters respectively.

The image processing unit 124 is configured to receive a first and a second main-shot image corresponding to the first and the second main-shot X-ray beam respectively from the X-ray detector 140. In the above example, the image processing unit 124 receives a low energy main-shot image (i.e., a first main-shot image) corresponding to the low energy main-shot X-ray beam and a high energy main-shot image (i.e., a second main-shot image) corresponding to the high energy main-shot X-ray beam. The image processing unit 124 then generates a final image (e.g., a bone image, a soft tissue image, and the like) of the object based on the first and the second main-shot image. In one embodiment, the image processing unit 124 generates the final image by determining a difference between the first and the second main shot images (i.e., subtracting the first main-shot image from the second main-shot image or subtracting the second main-shot image from the first main-shot image). In a further embodiment, the image processing unit 124 generates the final image by determining a difference between the first and the second main-shot images based on a weighting factor. The image processing unit 124 receives the weighting factor from the X-ray detector 140. The weighting factor is described in further detail with reference to FIG. 2.

The image processing unit 124 may be further configured to generate graphical data for providing a user interface including the final image of the object to, for example, an operator of the system 100. The image processing unit 124 then sends the graphical data to a display device (not shown) coupled to the system controller 120. The display device (not shown) renders the graphical data and displays the user interface. Although, in the illustrated embodiment, the image processing unit 124 is included in the system controller 120, in other embodiments the image processing unit 124 may be included in the X-ray detector 140 or in a separate computing device.

The X-ray detector 140 may be any type of device configured to generate a pre-shot image of a patient, determine the first and the second main-shot parameters, and generate the first and the second main-shot images of the patient. In the illustrated system 100, the X-ray detector 140 is a portable X-ray detector (e.g., detector of a mobile RAD system) that includes a detection circuitry 150 and a parameter optimizer 160. The detection circuitry 150 may be any type of device configured to receive X-ray photons of the pre-shot X-ray beam, the first main-shot X-ray beam, and the second main-shot X-ray beam and generate the pre-shot image, the first main-shot image, and the second main-shot image respectively. The detection circuitry 150 may include for example, photostimulable phosphor plates, semiconductor detectors, scintillators, flat panel detectors, and the like. The detection circuitry 150 is configured to send the first and the second main-shot images to the image processing unit 124. The detection circuitry 150 is further configured to send the pre-shot image and the first main-shot image to the parameter optimizer 160 via signal line 155. The parameter optimizer 160 may be any type of computing device configured to determine and send the first and the second main-shot parameters to the source controller 122 via the network 130. The parameter optimizer 160 is described below in further detail with reference to FIG. 2.

The network 130 may be a wired or a wireless type network, and may have any number of configurations such as a star configuration, token ring configuration, or other known configurations. Furthermore, the network 130 may include a local area network (LAN), a wide area network (WAN) (e.g., the internet), and/or any other interconnected data path across which multiple devices may communicate. In one embodiment, the network 130 may be a peer-to-peer network. The network 130 may also be coupled to or include portions of a telecommunication network for sending data in a variety of different communication protocols. In another embodiment, the network 130 includes Bluetooth communication networks or a cellular communications network for sending and receiving data such as via a short messaging service (SMS), a multimedia messaging service (MMS), a hypertext transfer protocol (HTTP), a direct data connection, WAP, email, or the like. While only one network 130 is shown coupled to the X-ray detector 140 and the system controller 120, multiple networks 130 may be coupled to the entities.

Figure 2:
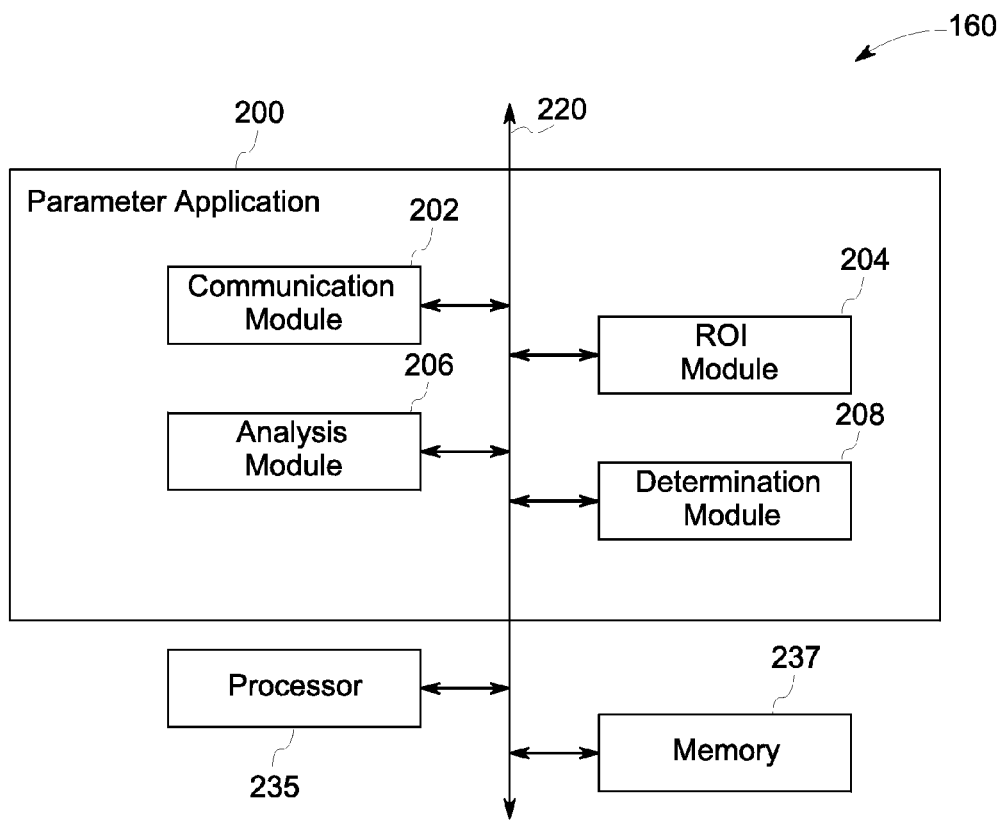
FIG. 2 is a block diagram illustrating a parameter optimizer according to one embodiment.

FIG. 2 is a block diagram illustrating the parameter optimizer 160 according to one embodiment. The parameter optimizer 160 includes a parameter application 200, a processor 235, and a memory 237. The parameter application 200 includes a communication module 202, a region of interest (ROI) module 204, an analysis module 206, and a determination module 208. The modules of the parameter application 200, the processor 235, and the memory 237 are coupled to a bus 220 for communication with one another.

The processor 235 may include at least one arithmetic logic unit, microprocessor, general purpose controller or other processor arrays to perform computations, and/or retrieve data stored on the memory 237. In another embodiment, the processor 235 is a multiple core processor. The processor 235 processes data signals and may include various computing architectures including a complex instruction set computer (CISC) architecture, a reduced instruction set computer (RISC) architecture, or an architecture implementing a combination of instruction sets. The processing capability of the processor 235 may be limited to supporting the retrieval of data and transmission of data. The processing capability of the processor 235 may also perform more complex tasks, including various types of feature extraction, modulating, encoding, multiplexing, or the like. In other embodiments, other type of processors, operating systems, and physical configurations are also envisioned.

The memory 237 may be a non-transitory storage medium. For example, the memory 237 may be a dynamic random access memory (DRAM) device, a static random access memory (SRAM) device, flash memory or other memory devices. In one embodiment, the memory 237 also includes a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memories (DVD-RAM) device, a digital versatile disc rewritable (DVD-RW) device, a flash memory device, or other non-volatile storage devices.

The memory 237 stores data that is required for the parameter application 200 to perform associated functions. In one embodiment, the memory 237 stores the modules (e.g., the communication module 202, the analysis module 206, and the like) of the parameter application 200. In another embodiment, the memory 237 stores the pre-shot parameters, for example, the pre-shot kVp, the distance between the X-ray source 110 and the X-ray detector 140, the patient size, and the like.

The communication module 202 includes codes and routines configured to handle communication between the system controller, the detection circuitry, and the modules of the parameter application 200. In one embodiment, the communication module 202 includes a set of instructions executable by the processor 235 to provide the functionality for handling communication between the system controller, the detection circuitry, and the modules of the parameter application 200. In another embodiment, the communication module 202 is stored in the memory 237 and is accessible and executable by the processor 235. In either embodiment, the communication module 202 is adapted for communication and cooperation with the processor 235 and other modules of the parameter application 200 via the bus 220.

In one embodiment, the communication module 202 receives the pre-shot parameters from the source controller and sends the pre-shot parameters to the determination module 208. In another embodiment, the communication module 202 receives a pre-shot image and a first main-shot image from the detection circuitry and sends the pre-shot image and the first main-shot image to the ROI module 204 and the analysis module 206. In yet another embodiment, the communication module 202 receives a first and a second set of main-shot parameters from the determination module 208. The communication module 202 wirelessly sends the first set and the second set of main-shot parameters to the source controller via the network.

The ROI module 204 includes codes and routines configured to receive images from the detection circuitry generate one or more ROI images. In one embodiment, the ROI module 204 includes a set of instructions executable by the processor 235 to provide the functionality for receiving images from the detection circuitry and generating one or more ROI images. In another embodiment, the ROI module 204 is stored in the memory 237 and is accessible and executable by the processor 235. In either embodiment, the ROI module 204 is adapted for communication and cooperation with the processor 235 and other modules of the parameter application 200 via the bus 220.

The ROI module 204 receives the pre-shot image from the communication module 202 and determines one or more ROI in the pre-shot image. In one embodiment, the ROI module 204 may determine one or more ROI in the pre-shot image based on segmentation algorithms, for example, edge detection algorithms, region-based algorithms, clustering algorithms, histogram based algorithms, and the like. In another embodiment, the ROI module 204 determines one or more ROI in the pre-shot image based on ROI location data (e.g., x-y coordinates of the ROI within the pre-shot image) received from the source controller. In such an embodiment, the pre-shot parameters received from the source controller include the ROI location data. In yet another embodiment, the ROI module 204 determines one or more ROI in the pre-shot image based on segmentation algorithms in combination with ROI location data received from the source controller. In all embodiments, the ROI module 204 generates one or more ROI images of the pre-shot image by, for example, cropping the one or more ROI from the pre-shot image. Similarly, the ROI module 204 receives a first main-shot image from the communication module 202 and generates one or more ROI images of the first main-shot image. The ROI module 204 then sends the one or more ROI images of the pre-shot image and the first main-shot image to the analysis module 206. The one or more ROI images are described below in further detail with reference to FIG. 3.

The analysis module 206 includes codes and routines configured to analyze one or more ROI images of the pre-shot image and the first main-shot image and determine one or more image characteristics of the pre-shot image and first main-shot image respectively. In one embodiment, the analysis module 206 includes a set of instructions executable by the processor 235 to provide the functionality for analyzing the one or more ROI images of the pre-shot image and the first-main shot image and determine one or more image characteristics of the pre-shot image and the first main-shot image respectively. In another embodiment, the analysis module 206 is stored in the memory 237 and is accessible and executable by the processor 235. In either embodiment, the analysis module 206 is adapted for communication and cooperation with the processor 235 and other modules of the parameter application 200 via the bus 220.

The analysis module 206 analyzes the one or more ROI images received from the ROI module 204 and determines one or more image characteristics of the corresponding pre-shot image and the first main-shot image. The one or more image characteristics of the pre-shot image or the first main-shot image include a number of counts in the one or more ROI images, an average (e.g., arithmetic mean, weighted mean, median, and the like) of the counts in the one or more ROI images, a histogram of the counts, a noise level, a signal to noise ratio, a contrast level, a contrast to noise ratio, and the like.

A count of an ROI image is proportional to the intensity level (e.g., linearly, logarithmically, quadratically, and the like) of each pixel in the ROI image. The analysis module 206 determines the histogram of the counts for an ROI image by binning the number of counts associated with each pixel of the ROI images into multiple bins (e.g., two bins, three bins, 256 bins, 65000 bins, and the like). In one embodiment, the analysis module 206 determines the histogram of the counts by binning the counts of all the ROI images received from the ROI module 204 into the same number of bins. In another embodiment, the analysis module 206 determines the histogram of the counts by dynamically binning the counts of the ROI images based on, for example, the location of each ROI image within the pre-shot image or the first main-shot image, the intensity level of each ROI image, and the like. For example, the analysis module 206 receives two ROI images of a pre-shot image or the first main-shot image from the ROI module 204. In such an example, the analysis module 206 determines the histogram of the first and the second ROI image by binning the number of counts into 4 bins and 8 bins respectively, based on the location of the ROI images. The analysis module 206 is further configured to send the one or more image characteristics of the pre-shot image and the first main-shot image to the determination module 208.

In one embodiment, the analysis module 206 analyzes the one or more ROI images to determine a quality metric (e.g., intensity level of the pre-shot image, motion blur, and the like) of the pre-shot image. The analysis module 206 determines whether the quality metric satisfies a quality criterion (e.g., intensity threshold, motion threshold, and the like). The quality criterion is stored in the memory 237 and may be defined by, for example, an operator of the X-ray imaging system based on previously collected clinical data. In such an embodiment, the analysis module 206 determines the image characteristics of the pre-shot image in response to determining that the quality metric satisfies a quality criterion. The analysis module 206 sends a notification to the source controller for re-generating the pre-shot image in response to determining that the quality metric fails to satisfy the quality criterion. For example, the analysis module 206 determines that the average intensity level of the pre-shot image is less than the intensity threshold. In such an example, since the quality metric (i.e., average intensity level) fails to satisfy the quality criterion (i.e., intensity threshold), the analysis module 206 sends a notification to the source controller. The notification instructs an operator of the X-ray imaging system to re-take the pre-shot image by, for example, modifying the pre-shot parameters, re-positioning the patient relative to the X-ray detector, and the like. In another example, the analysis module 206 determines that the motion blur in the pre-shot image exceeds the motion threshold. In such an example, since the quality metric (i.e., motion blur) fails to satisfy the (i.e., motion threshold), the analysis module 206 sends a notification instructing the operator of the X-ray imaging system to re-take the pre-shot image.

Although, the analysis module 206 is described above as determining the quality metric and the image characteristics of the pre-shot image and the main-shot image based on the one or more ROI images, in one embodiment, the analysis module 206 may determine the quality metric and the image characteristics based on the pre-shot image and main-shot image. In such an embodiment, the analysis module 206 receives the pre-shot image and the main-shot image from the communication module 202.

The determination module 208 includes codes and routines configured to determine a first and a second set of main-shot parameters corresponding to the first and the second main-shot images respectively. In one embodiment, the determination module 208 includes a set of instructions executable by the processor 235 to provide the determining the first and the second set of main-shot parameters. In another embodiment, the determination module 208 is stored in the memory 237 and is accessible and executable by the processor 235. In either embodiment, the determination module 208 is adapted for communication and cooperation with the processor 235 and other modules of the parameter application 200 via the bus 220.

The determination module 208 receives the pre-shot parameters and the image characteristics from the communication module 202 and the analysis module 206 respectively. In one embodiment, the determination module 208 calculates the first and the second set of main-shot parameters based on the pre-shot parameters and the image characteristics of the pre-shot image. For example, the determination module 208 calculates the first and the second main-shot kVp and the first and the second main-shot mAs based on the number of counts in the pre-shot image or the one or more ROI images, the pre-shot mAs, the pre-shot kVp, the patient size, and the distance between the X-ray source and the X-ray detector. In another example, the determination module 208 determines the first and the second main-shot kVp, the first and the second main-shot exposure times, the first and the second main-shot X-ray focal spot sizes, and the first and the second main-shot X-ray filters based on a look-up table stored in the memory 237 and defined by, for example, an operator of the X-ray imaging system. In such an example, the look-up table includes, for example, the pre-shot kVp, the pre-shot mAs, the patient size, the anatomical region of the patient, the view type, an intended target of optimization (e.g., bone, soft tissue, and the like), the image characteristics, and the like.

In another embodiment, the determination module 208 calculates the first set of main-shot parameters based on the pre-shot parameters and the image characteristics of the pre-shot image. The determination module 208 further receives image characteristics of the first main-shot image corresponding to the first set of main-shot parameters from the analysis module. In such an embodiment, the determination module calculates the second set of main-shot parameters based on at least one of the pre-shot parameters, the image characteristics of the pre-shot image, and the image characteristics of the first main-shot image. For example, the determination module 208 calculates the second main-shot kVp and the second main-shot mAs based on the number of counts in the pre-shot image, the number of counts in the first main-shot image, the pre-shot mAs, the pre-shot kVp, the patient size, and the distance between the X-ray source and the X-ray detector.

The determination module 208 is further configured to calculate a weighting factor for determining the final image of the object. The weighting factor may be linear or non-linear. In one embodiment, the determination module 208 calculates the weighting factor based on the pre-shot parameters and the image characteristics of the pre-shot image. For example, the determination module 208 calculates the weighting factor based at least on the patient size and the number of counts in the pre-shot image. In another embodiment, the determination module 208 calculates the weighting factor based on at least one of the pre-shot parameters, the image characteristics of the pre-shot image, and the image characteristics of the first main-shot image. For example, the determination module 208 calculates the weighting factor based at least on the patient size, the distance between the X-ray source and the X-ray detector, the number of counts in the pre-shot image, and the number of counts in the first main-shot image. In yet another embodiment, the determination module 208 calculates the weighting factor based on at least one of the pre-shot parameters, the image characteristics of the pre-shot image, the image characteristics of the first main-shot image, and the image characteristics of the second main-shot image. In such an embodiment, the analysis module 206 determines the image characteristics of the second main-shot image by analyzing the second main-shot image similar to analysis of the first main-shot image. The determination module 208 receives the image characteristics of the second main-shot image from the analysis module 206.

The determination module 208 is also configured to wirelessly send the first and the second set of main-shot parameters to the source controller via the network. The source controller then instructs the X-ray source to project a first and a second main-shot X-ray beam based on the received main-shot parameters, for generating the first and the second main-shot image of the patient respectively. The determination module 208 is also configured to wirelessly send the weighting factor to the image processing unit. The image processing unit then determines the final image of the object based on the first main-shot image, the second main-shot image, and the weighting factor. The determination of the weighting factor based on the image characteristics of the pre-shot image and/or the first main-shot image is advantageous as it reduces the errors and improves the quality of the final image of the object.

In X-ray imaging systems, for example, mobile RAD systems, wirelessly sending the main-shot parameters is faster than sending the pre-shot image due to the large size of the pre-shot image and the network's slow data transmission speeds. Thus, wirelessly sending the main-shot parameters is advantageous as it significantly reduces the time delay between generating the pre-shot image and the main-shot image and reduces the inconvenience experienced by the patient while generating the X-ray image. In one embodiment, the determination module 208 is further configured to wirelessly send the one or more image characteristics and the ROI images to the source controller along with the one or more main-shot parameters. In another embodiment, the determination module 208 is further configured to generate a new image by reducing the spatial resolution (i.e., the size) of the pre-shot image and wirelessly send the new image to the source controller. In such an embodiment, the determination module 208 generates the new image by processing the pre-shot image using a Gaussian filter, a weighted median filter, and the like. Although the determination module 208 is described above as wirelessly sending the main-shot parameters, the one or more image characteristics, the one or more ROI images, and the like to the source controller, in one embodiment, the determination module 208 may send the data to the source controller via a wired network.

Figure 3:
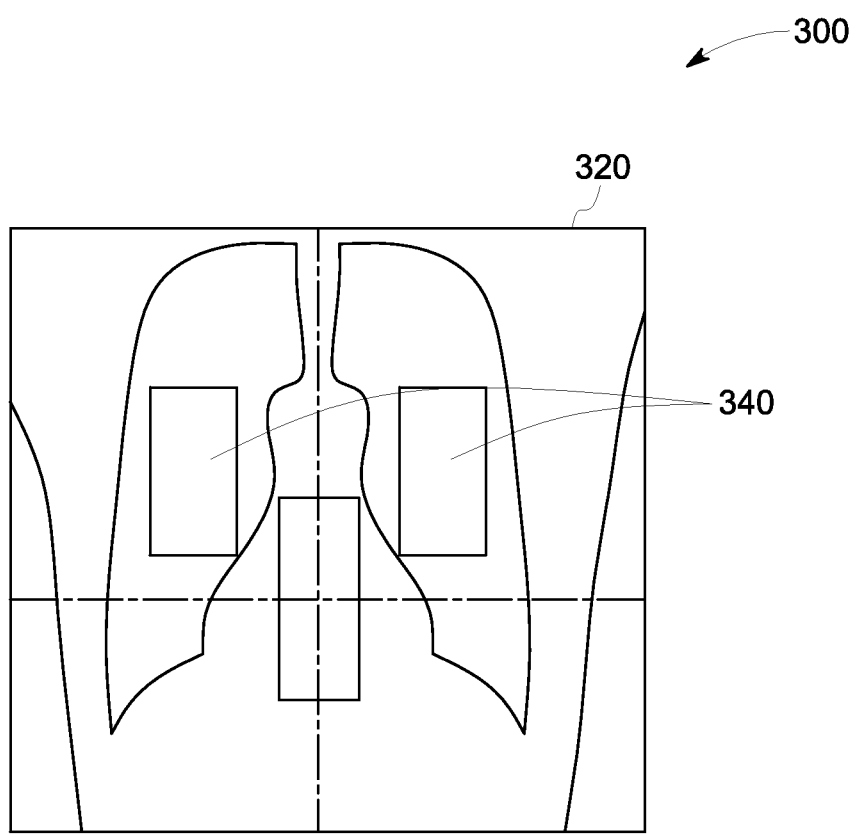
FIG. 3 is a graphical representation of a pre-shot image according to one embodiment.

FIG. 3 illustrates a graphical representation 300 of a pre-shot image 320 received according to one embodiment. The pre-shot image 320 is an image of a human chest. In the illustrated embodiment, the ROI module determines two ROI 340 within the pre-shot image 320. The ROI module then generates and sends two ROI images to the analysis module.

Figure 4:
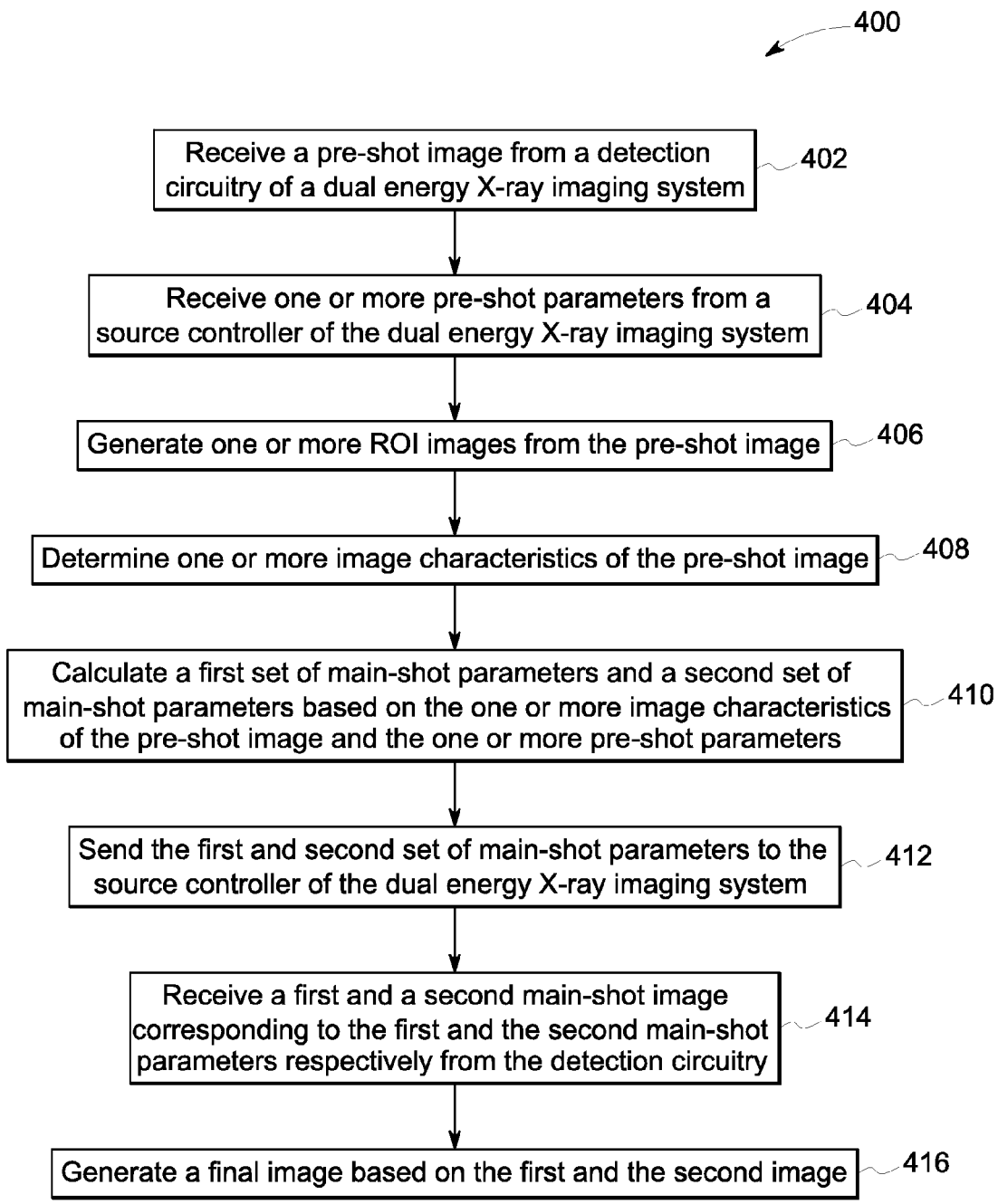
FIG. 4 is a flow diagram illustrating a method for determining X-ray exposure parameters according to one embodiment.

FIG. 4 is a flow diagram illustrating a method for determining main-shot parameters according to one embodiment. The communication module receives a pre-shot image from a detection circuitry of a dual energy X-ray imaging system 402. The communication module also receives one or more pre-shot parameters from a source controller of the dual energy X-ray imaging system 404. For example, the communication module receives the pre-shot kVP, the pre-shot mAs, the patient size, and the distance between the X-ray source and the X-ray detector. The ROI module generates one or more ROI images from the pre-shot image 406. The analysis module determines one or more image characteristics of the pre-shot image 408. For example, the analysis module determines an average of the counts and the histogram of the counts in the one or more ROI images. The determination module calculates a first set of main-shot parameters and a second set of main-shot parameters based on the one or more image characteristics of the pre-shot image and the one or more pre-shot parameters 410. For example, the determination module calculates a first main-shot mAs, a second main-shot mAs, a first main-shot kVp, and a second main-shot kVp based on the average of the counts in the pre-shot image, the histogram of the counts in the pre-shot image, the pre-shot kVp, the pre-shot mAs, and the patient size.

The determination module then sends the first and the second main-shot parameters to the source controller of the dual energy X-ray imaging system 412. The image processing unit then receives a first and second main-image corresponding to the first and the second main-shot parameters respectively from the detection circuitry 414. The image processing unit generates a final image based on the first and the second main-shot image 416. For example, the image processing unit generates a bone image of an object by a weighted subtraction the first main-shot image from the second main-shot image.

Figure 5:
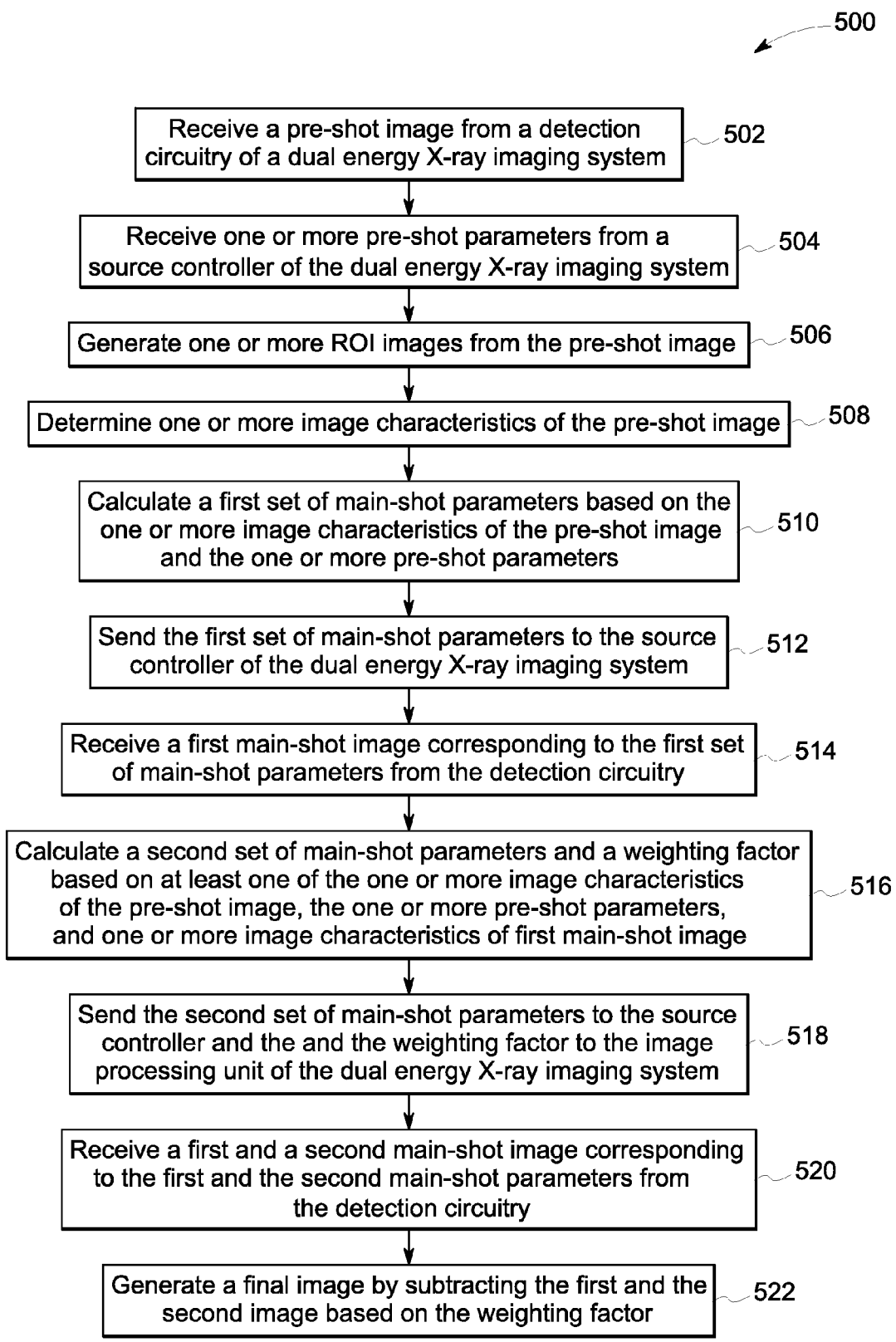
FIG. 5 is flow diagram illustrating another method for determining X-ray exposure parameters according to one embodiment.

FIG. 5 is a flow diagram illustrating a method for determining main-shot parameters according to another embodiment. The communication module receives a pre-shot image from a detection circuitry of a dual energy X-ray imaging system 502. The communication module also receives one or more pre-shot parameters from a source controller of the dual energy X-ray imaging system 504. The ROI module generates one or more ROI images from the pre-shot image 506. The analysis module determines one or more image characteristics of the pre-shot image 508. The determination module calculates a first set of main-shot parameters based on the one or more image characteristics of the pre-shot image and the one or more pre-shot parameters 510. The determination module sends the first set of main-shot parameters to the source controller of the dual energy X-ray imaging system 512. The communication module then receives a first main-shot image corresponding to the first set of main-shot parameters from the detection circuitry 514. The determination module then calculates a second set of main-shot parameters and a weighting factor based on at least one of the pre-shot parameters, the one or more image characteristics of the pre-shot image, and the one or more image characteristics of the main-shot image 516. For example, the determination module calculates a second main-shot mAs, a second main-shot kVp, and the weighting factor based on the average of the counts of the pre-shot image, the histogram of the counts of the first main-shot image, the pre-shot kVp, the pre-shot mAs, and the patient size. In such an example, the determination module receives the histogram of the counts of the first main-shot image from the analysis module.

The determination module then sends the second main-shot parameters to the source controller and the weighting factor to the image processing unit of the dual energy X-ray imaging system 518. The image processing unit then receives the first and the second main-image corresponding to the first and the second main-shot parameters respectively from the detection circuitry 520. The image processing unit generates a final image based on the first main-shot image, the second main-shot image, and the weighting factor 522. For example, the image processing unit generates a soft tissue image of an object by subtracting the first main-shot image from the second main-shot image based on the weighting factor.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A dual energy X-ray imaging system comprising:
a detection circuitry configured to generate a pre-shot image based on a pre-shot X-ray beam; and
a parameter optimizer communicatively coupled to the detection circuitry and configured to determine a first set of main-shot parameters and a second set of main-shot parameters, the parameter optimizer comprising:
at least one processor;
a communication module stored in a memory and executable by the at least one processor, the communication module configured to receive the pre-shot image from the detection circuitry and receive one or more pre-shot parameters from a source controller of the dual energy X-ray imaging system;
an analysis module stored in the memory and executable by the at least one processor, the analysis module communicatively coupled with the communication module and configured to determine one or more image characteristics of the pre-shot image, wherein the one or more image characteristics includes at least one of a histogram of counts of intensity levels of pre-shot image pixels, a noise level, a signal to noise ratio, a contrast, and a contrast to noise ratio; and
a determination module stored in the memory and executable by the at least one processor, the determination module communicatively coupled with the analysis module and configured to calculate the first and the second set of main-shot parameters based on the one or more pre-shot parameters and the one or more image characteristics of the pre-shot image, and send the first and the second set of main-shot parameters to the source controller of the dual energy X-ray imaging system.

2. The dual energy X-ray imaging system of claim 1, further comprising an image processing unit configured to receive a first main-shot image corresponding to the first set of main-shot parameters, receive a second main-shot image corresponding to the second set of main-shot parameters, and generate a final image based on the first and the second main-shot images.

3. The dual energy X-ray imaging system of claim 2, wherein the determination module is further configured to calculate a weighting factor based on at least one of the pre-shot parameters, the one or more image characteristics of the pre-shot image, one or more image characteristics of the first main-shot image, and one or more image characteristics of the second main-shot image.

4. The dual energy X-ray imaging system of claim 3, wherein the image processing unit is further configured to generate the final image based on the first main-shot image, the second main-shot image, and the weighting factor.

5. The dual energy X-ray imaging system of claim 1, wherein the one or more pre-shot parameters include at least one of a peak kilovoltage (kVp) of an X-ray source, a pre-shot milliampere seconds (mAs) of the X-ray source, x-ray focal spot size, a patient size, an anatomy, a view, and a distance between the X-ray source and an X-ray detector.

6. The dual energy X-ray imaging system of claim 1, wherein the first set of main-shot parameters includes at least one of a first main-shot mAs, a first main-shot mA, a first main-shot exposure time, a first main-shot kVp, a first main-shot x-ray focal spot size, and a first main-shot X-ray filter.

7. The dual energy X-ray imaging system of claim 1, wherein the second set of main-shot parameters includes at least one of a second main-shot mAs, a second main-shot mA, a second main-shot exposure time, a second main-shot kVp, a second main-shot x-ray focal spot size, and a second main-shot X-ray filter.

8. A computer-implemented method, comprising:
receiving a pre-shot image from a detection circuitry of a dual energy X-ray imaging system;
receiving one or more pre-shot parameters from a source controller of the dual energy X-ray imaging system;
determining one or more image characteristics of the pre-shot image includes at least one of a histogram of counts of intensity levels of pre-shot image pixels, a noise level, a signal to noise ratio, a contrast, and a contrast to noise ratio;
calculating a first set of main-shot parameters and a second set of main shot parameters based on the one or more pre-shot parameters and the one or more image characteristics of the pre-shot image; and
sending the first and the second set of main-shot parameters to the source controller of the dual energy X-ray imaging system.

9. The method of claim 8, further comprising:
receiving a first main-shot image corresponding to the first set of main-shot parameters and a second main-shot image corresponding to the second set of main-shot parameters; and
generating a final image based on the first and the second main-shot images.

10. The method of claim 8, wherein the one or more pre-shot parameters include at least one of a peak kilovoltage (kVp) of an X-ray source, a pre-shot milliampere seconds (mAs) of the X-ray source, x-ray focal spot size, a patient size, an anatomy, a view, and a distance between the X-ray source and an X-ray detector.

11. The method of claim 8, wherein the first set of main-shot parameters includes at least one of a first main-shot mAs, a first main-shot mA, a first main-shot exposure time, a first main-shot x-ray focal spot size, a first main-shot kVp, and a first main-shot X-ray filter.

12. The method of claim 8, wherein the second set of main-shot parameters includes at least one of a second main-shot mAs, a second main-shot mA, a second main-shot exposure time, a second main-shot x-ray focal spot size, a second main-shot kVp, and a second main-shot X-ray filter.

13. A computer-implemented method, comprising:
receiving a pre-shot image from a detection circuitry of a dual energy X-ray imaging system;
receiving one or more pre-shot parameters from a source controller of the dual energy X-ray imaging system;
determining one or more image characteristics of the pre-shot image includes at least one of a histogram of counts of intensity levels of pre-shot image pixels, a noise level, a signal to noise ratio, a contrast, and a contrast to noise ratio;
calculating a first set of main-shot parameters based on the one or more pre-shot parameters and the one or more image characteristics of the pre-shot image;

sending the first set of main-shot parameters to the source controller of the dual energy X-ray imaging system;

receiving a first main-shot image corresponding to the first set of main-shot parameters from the detection circuitry;

calculating a second set of main-shot parameters based on at least one of the pre-shot parameters, the one or more image characteristics of the pre-shot image, and one or more image characteristics of the first main-shot image; and sending the second set of main-shot parameters to the source controller of the dual energy X-ray imaging system.

14. The method of claim 13, further comprising calculating a weighting factor based on at least one of the pre-shot parameters, the one or more image characteristics of the pre-shot image, the one or more image characteristics of the first main-shot image, and one or more image characteristics of a second main-shot image corresponding to the second set of main-shot parameters.

15. The method of claim 14, further comprising:

receiving the second main-shot image corresponding to the second set of main-shot parameters; and generating a final image based on the first and the second main-shot images and the weighting factor.

16. The method of claim 13, wherein the one or more pre-shot parameters include at least one of a peak kilovoltage (kVp) of an X-ray source, a pre-shot milliampere seconds (mAs) of the X-ray source, x-ray focal spot size, a patient size, an anatomy, a view, and a distance between the X-ray source and an X-ray detector.

17. The method of claim 13, wherein the first set of main-shot parameters includes at least one of a first main-shot mAs, a first main-shot mA, a first main-shot exposure time, a first main-shot x-ray focal spot size, a first main-shot kVp, and a first main-shot X-ray filter.

* * * * *